US00PP09345P

United States Patent [19]

Zary

[11] Patent Number: Plant 9,345

[45] Date of Patent: Oct. 31, 1995

[54] HYBRID TEA ROSE PLANT NAMED 'JACRAL'

[75] Inventor: Keith W. Zary, Thousand Oaks, Calif.

[73] Assignee: Bear Creek Gardens, Inc., Medford, Oreg.

[21] Appl. No.: 316,898

[22] Filed: Oct. 3, 1994

[51] Int. Cl.[6] ..... A01H 5/00

[52] U.S. Cl. ..... Plt./20

[58] Field of Search ..... Plt./20, 21

[56] References Cited

U.S. PATENT DOCUMENTS

P.P. 4,767 9/1981 Warriner ..... Plt./20

P.P. 7,510 4/1991 Kordes ..... Plt./20

*Primary Examiner*—Howard J. Locker

*Attorney, Agent, or Firm*—Klarquist Sparkman Campbell Leigh & Whinston

[57] ABSTRACT

A Hybrid Tea rose plant having non-fading, bright red flowers, dark green, glossy, mildew resistant foliage, long stems, moderate fragrance, and good vase life.

1 Drawing Sheet

The present invention relates to a new and distinct variety of rose plant of the Hybrid Tea class which was originated by me by crossing the variety JACstop, U.S. Plant Pat. No. 6,971, with the variety JACreb (unpatented).

The primary objective of this breeding was to produce a new rose variety having the dark green, glossy, mildew resistant foliage of the female parent, combined with the large, bright red flower and long stems of the male parent. This objective was substantially achieved, along with other desirable improvements, as evidenced by the following unique combination of characteristics that are outstanding in the new variety and that distinguish it from its parents, as well as from all other varieties of which I am aware:

1. Non-fading, bright red flowers;
2. Dark green, glossy, mildew resistant foliage;
3. Long stems;
4. Moderate fragrance; and
5. Good vase life.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with the Royal Horticultural Society (London) Colour Chart, except where ordinary dictionary significance of color is indicated.

Parentage:

*Seed parent.*—JACstop (U.S. Plant Pat. No. 6,971).

*Pollen parent.*—JACreb.

Classification:

*Botanical.*—*Rosa hybrida.*

*Commercial.*—Hybrid tea.

FLOWER

Observations made from specimens grown in a greenhouse environment at Somis, Calif., from March to July 1994.

Blooming habit: Continuous.

Bud:

*Size.*—1¾ inches long when the petals start to unfurl.

*Form.*—The bud form is long, pointed ovoid.

*Color.*—When sepals first divide, bud color is Red Group 45A. When half blown, the upper sides of the petals are Red Group 45A; and the lower sides of the petals are Red Group 45A.

*Sepals.*—Color: Green Group 138C. Surface texture: Covered in fine hairs. There are three lightly to normally appendaged sepals. There are two unappendaged sepals with hairy edges.

*Receptacle.*—Color: Green Group 141C. Shape: Funnel. Size: Medium (⅜ inch×¼ inch). Surface: Smooth.

*Peduncle.*—Length: Medium (3½ inches). Surface: Glandular. Color: Medium green. Strength: Stiff, erect.

Bloom:

*Size.*—Large. Average open size is 4½ inches to 4¾ inches.

*Borne.*—Singly.

*Stems.*—Long. Average length is about 22 inches to 26 inches. Plant will produce about 180 stems per square meter per year.

*Form.*—When first open: High centered. Permanence: Flattens, outer petals curl back.

*Petalage.*—Number of petals under normal conditions: 30.

*Color.*—The upper side of the petals is Red Group 45A. The reverse side of the petals is Red Group 45A. The base of each petal has a small greenish white half moon at the point of attachment (⅛ inch×⅛ inch). The major color on the upper side is Red Group 45A.

*Variegations.*—Occasional green streak on the outer petals.

*Discoloration.*—The general tonality at the end of the first day: No change. At the end of the third day, no change, nor at the end of the fifth day.

*Fragrance.*—Moderate.

Petals:

*Texture.*—Thick, leathery.

*Shape.*—Round.

*Form.*—Tips slightly recurved.

*Arrangement.*—Imbricated, with no petaloids in the center.

*Persistence.*—Drop off cleanly.

*Lastingness.*—On the plant: Long (7 to 8 days). As a cut flower: Long (9 to 10 days).

Reproductive parts:

*Anthers.*—Size: Medium. Quantity: Many. Color: Yellow. Arrangement: Regular around styles.

*Filaments.*—Color: Reddish.

*Pollen.*—Color: Gold yellow.

*Styles.*—Color: Red.

*Stigmas.*—Color: Greenish white.

Form: Bush.

Growth: Vigorous, upright, branching. The height and width at one year in the greenhouse is 6 feet×4 feet.

Foliage:

*Number of leaflets on normal med-stem leaves*—5 or 7.

*Size.*—Large (6½ inches×5 inches).

*Quantity.*—Abundant.

*Color.*—New foliage: Greyed Red Group 178C. Old foliage: Green Group 139A on the upper side, and Green Group 139B on the lower side.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Rough, with prickles.

*Stipules.*—Medium (½ inch), smooth.

*Disease resistance.*—Resistant to mildew under normal greenhouse growing conditions in Somis, Calif.

Wood:

*New wood.*—Color: Reddish. Bark: Smooth.

*Old wood.*—Color: Green. Bark: Smooth.

Prickles:

*Quantity.*—On main canes from base: Many. On laterals from main canes: Many.

*Form.*—Medium (¼ inch), hooked downward.

*Color when young.*—Red.

Small prickles:

*Quantity.*—On main stalks: None. On laterals: None.

I claim:

1. A new and distinct variety of rose plant of the Hybrid Tea class, substantially as herein shown and described, characterized particularly as to novelty by the unique combination of its non-fading, bright red flowers, dark green, glossy, mildew resistant foliage, long stems, moderate fragrance, and good vase life.

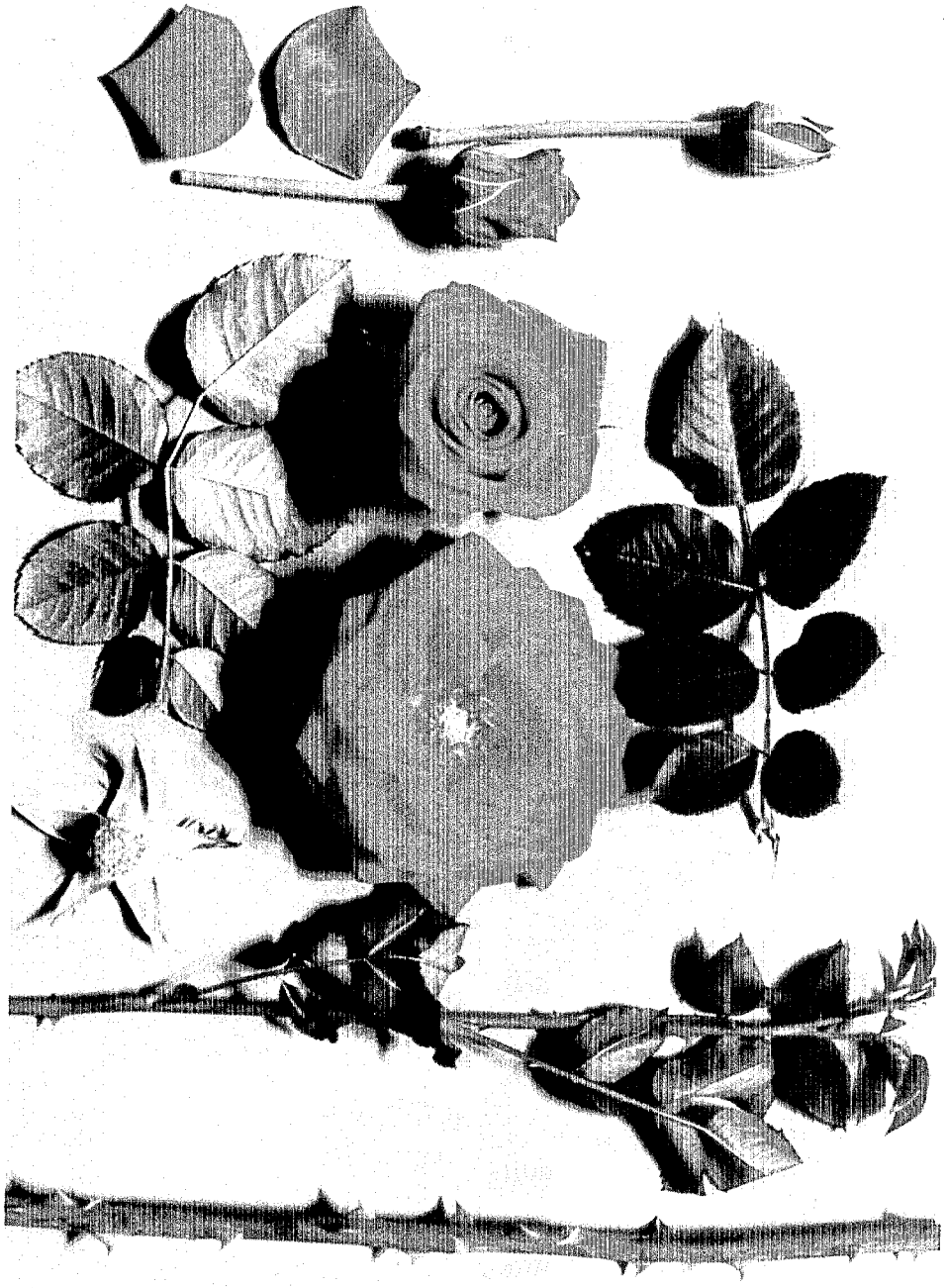

* * * * *